United States Patent
Hansen

(10) Patent No.: US 10,722,448 B2
(45) Date of Patent: Jul. 28, 2020

(54) PET CARE CLEANSING COMPOSITION

(71) Applicant: BOEHRINGER INGELHEIM ANIMAL HEALTH USA INC., Duluth, GA (US)

(72) Inventor: Eric Anthony Hansen, Atlanta, GA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/774,534

(22) PCT Filed: Nov. 9, 2016

(86) PCT No.: PCT/US2016/061048
§ 371 (c)(1),
(2) Date: May 8, 2018

(87) PCT Pub. No.: WO2017/083326
PCT Pub. Date: May 18, 2017

(65) Prior Publication Data
US 2019/0091133 A1    Mar. 28, 2019

Related U.S. Application Data

(60) Provisional application No. 62/252,958, filed on Nov. 9, 2015.

(51) Int. Cl.
| | | |
|---|---|---|
| *A61K 8/892* | (2006.01) |
| *A61K 8/34* | (2006.01) |
| *A61Q 5/02* | (2006.01) |
| *A61K 8/97* | (2017.01) |
| *A61Q 19/10* | (2006.01) |
| *A61Q 5/12* | (2006.01) |
| *A01N 65/08* | (2009.01) |
| *A61K 8/9794* | (2017.01) |
| *A61K 8/9789* | (2017.01) |
| *A61K 8/33* | (2006.01) |
| *A61K 8/49* | (2006.01) |
| *A61K 8/67* | (2006.01) |

(52) U.S. Cl.
CPC .............. *A61K 8/892* (2013.01); *A01N 65/08* (2013.01); *A61K 8/33* (2013.01); *A61K 8/345* (2013.01); *A61K 8/4973* (2013.01); *A61K 8/678* (2013.01); *A61K 8/97* (2013.01); *A61K 8/9789* (2017.08); *A61K 8/9794* (2017.08); *A61Q 5/02* (2013.01); *A61Q 5/12* (2013.01); *A61Q 19/10* (2013.01); *A61K 2800/30* (2013.01); *A61K 2800/33* (2013.01); *Y02A 50/322* (2018.01)

(58) Field of Classification Search
CPC .......... A61K 8/345; A61K 8/892; A61K 8/97; A61K 8/33; A61K 8/9789; A61K 8/9794; A61K 8/678; A61K 8/4973; A61K 2800/33; A61K 2800/30; A61Q 5/12; A61Q 19/10; A61Q 5/02; A01N 65/08; Y02A 50/322
See application file for complete search history.

(56) References Cited

U.S. PATENT DOCUMENTS

2008/0194642 A1* 8/2008 Albright ................ A01N 25/00
514/341
2009/0291057 A1* 11/2009 Chang .................... A61K 8/463
424/70.21

OTHER PUBLICATIONS

Diaz et al., ("Introduction to Ectoparasitic Diseases" in Mandell, Douglas, and Bennett's Principles and Practice of Infectious Disease (Eight Edition), vol. 2, 2015).*

* cited by examiner

*Primary Examiner* — Blessing M Fubara
(74) *Attorney, Agent, or Firm* — Judy Jarecki-Black; Richard Seeger

(57) ABSTRACT

A method of treating the skin or hair on a dog containing an effective amount of an ectoparasiticide previously applied to the skin or hair, comprising applying a quantity of a cleansing composition directly to the skin or hair, wherein the treatment does not result in reducing the efficacy of the ectoparasiticide against adult fleas (*C. felis*) or adult ticks (*R. sanguineus*) below 90% efficacy for at least a month after application of the ectoparasiticide; wherein the cleansing composition comprises about 1-3% glycerin; about 2-4% silicone copolyol esters, water and is essentially free of surfactant.

15 Claims, No Drawings

PET CARE CLEANSING COMPOSITION

CROSS-REFERENCE TO RELATED APPLICATIONS

This application claims priority to U.S. Provisional Application Ser. No. 62/252,958 filed 9 Nov. 2015, the disclosure of which is incorporated by reference in its entirety.

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention.

FIELD OF THE INVENTION

The present disclosure generally relates to non-rinse pet care compositions for conditioning, strengthening, cleansing and/or moisturizing the pet's keratin, wherein the composition is essentially free of surfactants and methods related thereto.

BACKGROUND OF THE INVENTION

Pet care products, for example shampoos, skin cleansers and moisturisers, often have the following drawbacks: firstly, the ingredients in the composition can be irritating to the skin or eyes (in the event, for example, that shampoo composition is washed into the eyes during rinsing); secondly, because the detergent action of a shampoo containing large amounts of surfactant generally removes oil soluble materials from the haircoat, it has heretofore been believed that these types of shampoos remove topical ectoparasiticides previous applied to the coat of the animal, making the ectoparasiticides ineffective when rinsed (Allen et al, U.S. Pat. No. 4,668,666); and thirdly, the pet products can leave the pet's coat dull and rough.

SUMMARY OF THE INVENTION

It is an object of the present invention to provide pet care compositions which are not irritating or which cause very little irritation to the pet's skin and to the eyes. It is also an object of the present invention to provide a pet cleansing composition which does not reduce the efficacy of previously applied ecoparasides on the pet's coats after several washings, while causing the coat to be fresh, clean, pleasant feeling and good smelling.

Accordingly, it is an object of the invention is to provide a method of treating kerarin material on pets, and kits thereof, using a composition of the invention.

The invention in its particular features will become more apparent from the following detailed description considered with reference to the accompanying examples. The following description will continue to discuss the problems and solutions offered by the present invention as they pertain to cosmetic applications.

DETAILED DESCRIPTION OF THE INVENTION

Terms used herein will have their customary meaning in the art unless specified otherwise.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "and/or" as used herein refers to and encompasses any and all possible combinations of one or more of the associated listed items.

The term "cosmetically acceptable carrier' as used herein includes any vehicle or base which is capable of delivering a composition of the invention to keratinous areas of the body for use as a cosmetic. Preferably the cosmetically acceptable carrier is water.

The term "cosmetically acceptable excipient" as used herein means any ingredient/compound or mixture of ingredients/compounds or compositions that is conventionally used to produce other desirable effects in pet care compositions to be applied to keratinous areas of the body. The preferred cosmetically acceptable excipients include but not limited to absorbents, amino acids, antioxidants, anti-static agents, anti-frizz agents, anti-dandruff agents, botanicals, botanical extracts, buffers, salts, chelating agents, conditioning agents, cosmetic oils, detergents, dyes, emollients, emulsifying agents, fillers, film formers, foam enhancers, fragrances, gelling agents, hair coloring agents, hair waving agents, hair straightening agents, humectants, lubricants, moisturizing agents, opacifying agents, pearlizers, pH adjusting agents, plant extracts, plant derivatives, plant tissue extracts, plant seed extracts, plant oils, preservatives, propellants, proteins, reducing agents, relaxers, sequestering agents, solubilizers, solvents, sunscreen agents, surfactants, thickening agents, viscosity modifiers, vitamins, volatiles, and combinations thereof.

The term "ectoparasiticide" as used herein refers to an agent that is capable of preventing, reducing or eliminating ectoparasite infestations. Preferred ectoparasiticides of the present invention include metaflumizone, amitraz, methoprene, permethrin, pyriproxyfen, moxidectin, demiditraz, fipronil, fluralaner, afoxalaner, sarolaner, lotilaner, pyriprole, dinotefuran and imidacloprid. The term "effective amount" as used herein in the context of an ectoparasiticide, refers to a sufficient amount of the ectoparasiticide to eradicate or reduce the number of parasites infesting the animal. In some embodiments, an effective amount of the active agent achieves at least 70% efficacy against the target parasite. In other embodiments, an effective amount of the active agent achieves at least 80%, or at least 90% efficacy against the target pests. Preferably, an effective amount of the active agent will achieve at least 95%, at least 98% or 100% efficacy against the target parasites.

The term "emollient" as used herein refers to an agent that is capable of softening and soothing the keratin materials when applied locally.

The term "essential oil" as used herein refers to a volatile oil derived from the leaves, stem, flower or twigs of plants or synthetically-made compounds that have the same chemical attributes. The essential oil usually carries the odor or flavor of the plant. Chemically, each plant essential oil or derivative thereof, which may be extracted from natural sources or synthetically made, generally contains, as a major constituent, an acyclic monoterpene alcohol or aldehyde, a benzenoid aromatic compound containing at least one oxygenated substituent or side chain, or a monocarbocyclic terpene generally having a six-membered ring bearing one or more oxygenated substituents. As used herein, "essential oil" includes derivatives thereof, including racemic mixtures, enantiomers, diastereomers, hydrates, salts, solvates, metabolites, analogs, and homologs.

The terms "essentially free of surfactant" and "essentially surfactant free" as used herein means that, while it is preferable that no surfactants be present in the composition, it is possible to have very small amounts of surfactants in the composition of the invention, provided that these amounts do not materially affect the advantageous properties of the composition. In particular, "essentially free of surfactant" means that the surfactants can be present in the composition at an amount of less than about 2.0% by weight, typically less than about 1.5% by weight, typically less than about 1.0% by weight, typically less than about 0.5% by weight, typically less than about 0.1% by weight, and more typically 0% by weight, based on the total weight of the composition.

The term "humectant" as used herein is considered synonymous with the term "moisturizing agent" and refers to a substance designed to make softer and more pliable the keratin materials, by increasing the extent of its hydration.

The term "keratin material" as used herein means the skin, the nails, paw pads or the keratin containing fibers such as hair, and fur.

The terms "keratin material conditioner" and "hair conditioner" as used herein refer to a substance that improves the quality of the skin, paw pads or hair, respectively, such as improving softness, manageability and luster.

The term "non-rinse shampoo" is used herein to mean means a shampoo which requires little or no additional liquid for its operation.

The term "silicone copolyol esters" as used herein include, for example, those having from about 2 to about 10 dialkylsiloxane units preferably dimethylpolysiloxane units, having from about 2 to about 20 carbon atoms derived from a fatty acid, and having from about 5 to about 10 oxyalkylene groups. Such silicone copolyol esters include, for example, dimethicone isostearate such as Dimethicone PEG-7 isostearate which is commercially available, for example, from Noveon with a tradename Ultrasil DW18, and dimethicone olivate such as Dimethicone PEG-7 olivate which is commercially available, for example, from Noveon with a tradename Ultrasil DW-O. Preferably Dimethicone PEG-7 isostearate.

The term "surfactant" as used herein refers to a surface-active substance, i. e., a substance capable of reducing the surface tension of a liquid in which it is dissolved.

The term "viscosity adjusting agent" as used herein is defined as a substance substantially altering a viscosity of a liquid composition compared to the viscosity of the composition in the absence of such substance.

It is further noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Embodiments of the present invention as described in the Summary of the Invention include those described below.

Embodiment 1

A pet care composition comprising *Verbascum thapsus* extract and a cosmetically acceptable carrier, which is essentially free of surfactant.

Embodiment 2

A pet care composition according to Embodiment 1 further comprising rhamnose, glucose and glucuronic acid.

Embodiment 3

A pet care composition according to Embodiment 1 wherein the total amount of *Verbascum thapsus* extract is from about 0.01% to about 0.2% by weight based on the total weight of the composition.

Embodiment 4

A pet care composition according to Embodiment 2 wherein the total amount of rhamnose, glucose and glucuronic acid is about 0.001 to about 1% by weight based on the total weight of the composition.

Embodiment 5

A pet care composition according to any one of Embodiments 1 to 4 further comprising a cosmetically acceptable excipient.

Embodiment 6

A pet care composition according to any one of Embodiments 1 to 5 further comprising Caprylyl Glycol and Ethylhexylglycerin (1,2-Propanediol, 3-[(2-ethylhexyl)oxy]).

Embodiment 7

A pet care composition according to any one of Embodiments 1 to 6 further comprising *Pisum sativum* sprout extract.

Embodiment 8

A pet care composition according to any one of Embodiments 1 to 7 further comprising Saccharide Isomerate (Psicose, Mannose, Fructose, Glucose and Galactose).

Embodiment 9

A pet care composition according to any one of Embodiments 1 to 8 further comprising Zinc Pyrithione.

Embodiment 10

A pet care composition according to any one of Embodiments 1 to 9 further comprising *Epilobium angustifolium*

Flower/Leaf/Stem Extract, *Tropaeolum majus* Flower/Leaf/Stem Extract, *Terminalia chebula* Bark Extract, and *Porphyridium cruentum* Extract.

Embodiment 11

A pet care composition according to any one of Embodiments 1 to 10 further comprising glycolic extract from active ingredients of *Krameria triandr, Sarothamnus scoparius* Koch (Giesta), *Juglans regia* L. (Indian Walnut).

Embodiment 12

A pet care composition according to any one of Embodiments 1 to 11 further comprising Biosaccharide gum-2 (rhamnose (I, III, VI), galactose (II, V) and glucuronic acid (IV)).

Embodiment 13

A pet care composition according to any one of Embodiments 1 to 12 further comprising Inca Inchi seeds oil (*Plukenetia volúbilis* Linneo).

Embodiment 14

A pet care composition according to Embodiment 13 wherein the Inca Inchi seeds oil comprises >99% vegetable oil being >80% polyunsaturated fatty acids, ≤10% monounsaturated fatty acids and <10% saturated fatty acids.

Embodiment 15

A pet care composition according to any one of Embodiments 1 to 14 further comprising *Moringa oleifera* Seed Extract, and *Moringa pterygosperma* Seed Extract.

Embodiment 16

A pet care composition according to any one of Embodiments 1 to 15 further comprising one or more plant extracts selected from the group consisting of Coconut Extract, Rosemary Extract, *Aloe vera* Extract, *Arnica* Extract, *Echinacea* Extract, and Horsetail Extract.

Embodiment 17

A pet care composition according to any one of Embodiments 1 to 16 further comprising dimethicone PEG-7 isostearate (Silsense DW-18).

Embodiment 18

A pet care composition according to any one of Embodiments 1 to 17 further comprising Citral.

Embodiment 19

A pet care composition according to any one of Embodiments 1 to 18 further comprising γ-Nonalactone.

Embodiment 20

A pet care composition according to any one of Embodiments 1 to 19 further comprising Zinc Oxide.

Embodiment 21

A pet care composition according to any one of Embodiments 1 to 20 further comprising Panthenol.

Embodiment 22

A pet care composition according to any one of Embodiments 1 to 21 further comprising Zinc Sulphate.

Embodiment 23

A pet care composition according to any one of Embodiments 1 to 22 further comprising cocamidopropyl betaine, sodium cocoamphoacetate, disodium laureth sulfosuccinate, glycerin, sodium chloride, laureth-2, peg/ppg-120/10 trimethylolpropane trioleate, phenoxyethanol, panthenol, propanediol, chlorphenesin, fragrance, citric acid, ethylhexylglycerin, sodium benzoate, polyquaternium-39, rhamnose, glucose, glucuronic acid, and potassium sorbate; and wherein the cosmetically acceptable carrier is water.

Embodiment 24

A pet care composition according to any one of Embodiments 1 to 23 further comprising cocamidopropyl betaine, sodium cocoamphoacetate, disodium laureth sulfosuccinate, glycerin, sodium chloride, laureth-2, peg/ppg-120/10 trimethylolpropane trioleate, phenoxyethanol, panthenol, propanediol, chlorphenesin, fragrance, citric acid, ethylhexylglycerin, sodium benzoate, polyquaternium-39, rhamnose, glucose, glucuronic acid, potassium sorbate, *Juglans regia* (walnut) leaf extract, *Krameria triandra* root extract, and *Sarothamnus scoparius* extract; and wherein the cosmetically acceptable carrier is water.

Embodiment 25

A pet care composition according to any one of Embodiments 1 to 24 further comprising cocamidopropyl betaine, sodium cocoamphoacetate, disodium laureth sulfosuccinate, glycerin, sodium chloride, laureth-2, peg/ppg-120/10 trimethylolpropane trioleate, phenoxyethanol, panthenol, propanediol, chlorphenesin, fragrance, citric acid, ethylhexylglycerin, sodium benzoate, polyquaternium-39, rhamnose, glucose, glucuronic acid, potassium sorbate, and biosaccharide gum-2; and wherein the cosmetically acceptable carrier is water.

Embodiment 26

A pet care composition according to any one of Embodiments 1 to 25 further comprising glycerin, sodium chloride, phenoxyethanol, propanediol, chlorphenesin, fragrance, citric acid, ethylhexylglycerin, *Verbascum thapsus* extract, sodium benzoate, rhamnose, glucose, glucuronic acid, potassium sorbate, caprylyl/capryl glucoside, *Plukenetia volubilis* seed oil, and lysine; and wherein the cosmetically acceptable carrier is water.

Embodiment 27

A pet care composition according to any one of Embodiments 1 to 26 comprising

| Ingredient | Amount (% by weight based on the total weight of the composition.) |
|---|---|
| propanediol, water, rhamnose, glucose and glucuronic acid | about 1% |
| panthenol | about 1% |
| zinc oxide | about 1.5% |
| caprylyl glycol and ethylhexylglycerin (1,2-propanediol, 3-[(2-ethylhexyl)oxy]) | about 0.6% |

Embodiment 28

A pet care composition according to any one of Embodiments 1 to 26 comprising

| Ingredient | Amount (% by weight based on the total weight of the composition.) |
|---|---|
| propanediol, water, rhamnose, glucose and glucuronic acid | about 1% |
| glycerin and verbascum thapsus extract | about 0.2% |
| pisum sativum sprout extract, phenoxyethanol, and sodium benzoate | about 0.35% |

Embodiment 29

A pet care composition according to any one of Embodiments 1 to 26 comprising

| Ingredient | Amount (% by weight based on the total weight of the composition.) |
|---|---|
| macadamia oil | about 0.2% |
| saccharide isomerate (psicose, mannose, fructose, glucose and galactose) | about 0.7% |
| saccharide isomerate (psicose, mannose, fructose, glucose and galactose) | |
| propanediol, water, rhamnose, glucose and glucuronic acid | about 1% |
| glycerin and verbascum thapsus extract | about 0.1% |

Embodiment 30

A pet care composition according to any one of Embodiments 1 to 26 comprising

| Ingredient | Amount (% by weight based on the total weight of the composition.) |
|---|---|
| zinc pyrithione | about 0.1% |
| water, alcohol, glycerin, lecithin, maltodextrin, epilobium angustifolium flower/leaf/stem extract, tropaeolum majus flower/leaf/stem extract, terminalia chebula bark extract, porphyridium cruentum extract, hydroxyethylcellulose, guar hydroxypropyl trimonium chloride, tocopheryl acetate, and phenoxyethanol. | about 0.4% |
| propanediol, water, rhamnose, glucose and glucuronic acid | about 0.25% |
| glycerin and verbascum thapsus extract | about 0.05% |

Embodiment 31

A pet care composition according to any one of Embodiments 1 to 26 comprising

| Ingredient | Amount (% by weight based on the total weight of the composition.) |
|---|---|
| glycerin and verbascum thapsus extract | about 0.2% |
| propanediol, water, rhamnose, glucose and glucuronic acid | about 1% |
| panthenol | about 1% |
| glycolic extract from krameria triandr, sarothamnus scoparius koch (giesta), juglans regia 1. (indian walnut) | about 0.5% |

Embodiment 32

A pet care composition according to any one of Embodiments 1 to 26 comprising

| Ingredient | Amount (% by weight based on the total weight of the composition.) |
|---|---|
| propanediol, water, rhamnose, glucose and glucuronic acid | about 1% |
| glycerin and verbascum thapsus extract | about 0.2% |
| biosaccharide gum-2 (rhamnose (i, iii, vi), galactose (ii, v) and glucuronic acid (iv)) | about 1% |

Embodiment 33

A pet care composition according to any one of Embodiments 1 to 26 comprising

| Ingredient | Amount (% by weight based on the total weight of the composition.) |
|---|---|
| propanediol, water, rhamnose, glucose and glucuronic acid | about 1% |
| glycerin and verbascum thapsus extract | about 0.2% |
| inchi: lysine, sacha inchi (plukenetia volubilis) seed oil, tocopherol | about 0.4% |

Embodiment 34

A pet care composition according to any one of Embodiments 1 to 26 comprising

| Ingredient | Amount (% by weight based on the total weight of the composition.) |
|---|---|
| propanediol, water, rhamnose, glucose and glucuronic acid | about 1% |
| glycerin and verbascum thapsus extract | about 0.2% |
| moringa oleifera seed extract, moringa pterygosperma seed extract, and glyceryl laurate | about 0.5% |

Embodiment 35

A pet care composition according to any one of Embodiments 1 to 26 comprising

| Ingredient | Amount (% by weight based on the total weight of the composition.) |
|---|---|
| propanediol, water, rhamnose, glucose and glucuronic acid | about 1% |
| zinc sulphate | about 0.075% |

Embodiment 36

A pet care composition according to any one of Embodiments 1 to 26 comprising

| Ingredient | Amount (% by weight based on the total weight of the composition.) |
|---|---|
| panthenol | about 1% |
| zinc oxide | about 1.5% |
| propanediol, water, rhamnose, glucose and glucuronic acid | about 1% |

Embodiment 37

A pet care composition according to any one of Embodiments 1 to 26 comprising

| Ingredient | Amount (% by weight based on the total weight of the composition.) |
|---|---|
| glycerin and verbascum thapsus extract | about 0.2% |
| panthenol | about 1% |
| propanediol, water, rhamnose, glucose and glucuronic acid | about 1% |

Embodiment 38

A pet care composition according to any one of Embodiments 1 to 26 comprising

| Ingredient | Amount (% by weight based on the total weight of the composition.) |
|---|---|
| glycerin and verbascum thapsus extract | about 0.2% |
| zinc sulphate | about 0.1% |
| propanediol, water, rhamnose, glucose and glucuronic acid | about 1% |

Embodiment 39

A pet care composition according to any one of Embodiments 1 to 26 comprising

| Ingredient | Amount (% by weight based on the total weight of the composition.) |
|---|---|
| propanediol, water, rhamnose, glucose and glucuronic acid | about 1% |
| glycerin and verbascum thapsus extract | about 0.2% |
| lysine, sacha inchi (plukenetia volubilis) seed oil, tocopherol | about 0.4% |
| panthenol | about 1% |

Embodiment 40

A pet care composition according to any one of Embodiments 1 to 26 comprising

| Ingredient | Amount (% by weight based on the total weight of the composition.) |
|---|---|
| zinc pyrithione | about 0.1% |
| propanediol, water, rhamnose, glucose and glucuronic acid | about 1% |

Embodiment 41

A pet care composition according to any one of Embodiments 1 to 26 further comprising glycerin, silsense dw-18, citral, γ-nonalactone, coconut extract, rosemary extract, *Aloe vera* extract, *Arnica* extract, *Echinacea* extract, horsetail extract, and vitamin E.

Embodiment 42

A cleansing composition comprising about 1-3% glycerin; about 2-4% silicone copolyol esters; and a cosmetically acceptable carrier.

Embodiment 43

A cleansing composition according to Embodiment 42, wherein the cosmetically acceptable carrier is water.

Embodiment 44

A cleansing composition according to Embodiments 42 or 43 further comprising silsense dw-18.

Embodiment 45

A cleansing composition according to any one of Embodiments 42 to 44 further comprising citral.

Embodiment 46

A cleansing composition according to any one of Embodiments 42 to 45 further comprising γ-nonalactone.

Embodiment 47

A cleansing composition according to any one of Embodiments 42 to 46 wherein the cleansing composition is essentially free of surfactant.

Embodiment 48

A cleansing composition according to any one of Embodiments 42 to 47 wherein the cleansing composition does not contain an ectoparasiticide.

Embodiment 49

A cleansing composition comprising:

| Ingredient | Amount (% by weight based on the total weight of the composition.) |
| --- | --- |
| water | about 92% |
| glycerin | about 2% |
| dimethicone PEG-7 isostearate (Silsense DW-18) | about 3% |
| Citral | about 0.1% |
| γ-Nonalactone | about 0.2% |
| Coconut Extract | about 0.2% |
| Rosemary Extract | about 0.1% |
| Aloe Vera Extract | about 0.1% |
| Arnica Extract | about 0.1% |
| Echinacea Extract | about 0.1% |
| Horsetail Extract | about 0.1% |
| Vitamin E | about 0.1% |

Embodiment 50

A cleansing composition comprising:

| Ingredient | Amount (% by weight based on the total weight of the composition.) |
| --- | --- |
| Deionized Water | 92.152% |
| Glycerin | 2.048% |
| Silsense DW-18 | 3.584% |
| Citral | 0.030% |
| γ-Nonalactone | 0.160% |
| Coconut Extract | 0.160% |
| Rosemary Extract | 0.120% |
| Aloe Vera Extract | 0.030% |
| Arnica Extract | 0.030% |
| Echinacea Extract | 0.030% |
| Horsetail Extract | 0.030% |
| Vitamin E | 0.030% |

Embodiment 51

A cleansing composition according to any one of Embodiments 42 to 50 in the form of a conditioning shampoo and the like.

Embodiment 52

A cleansing composition according to any one of Embodiments 42 to 51 which is a liquid, semi-liquid, cream, foam, spray, lotion, or gel and is intended for topical application to the skin and/or hair of an animal.

Embodiment 53

A cleansing composition according to any one of Embodiments 42 to 52 which is a liquid, semi-liquid, foam, or spray.

Embodiment 54

A cleansing composition according to any one of Embodiments 42 to 53 which is a cleansing composition or foam.

Embodiment 55

A cleansing composition according to any one of Embodiments 42 to 54 which deodorizes for up to 14 days.

Embodiment 56

A cleansing composition according to any one of Embodiments 42 to 55 which deodorizes for up to 7 days.

Embodiment 57

A cleansing composition according to any one of Embodiments 42 to 56 wherein said cleansing composition has a freshness, cleanliness and pleasurableness value greater than 50 on a scale of from 1 to 100 after application to the dog.

Embodiment 58

A cleansing composition according to any one of Embodiments 42 to 57 wherein said cleansing composition is non-irritating to the skin and eyes.

Embodiment 59

A method of treating skin or hair on a dog, wherein the skin or hair contains an effective amount of an ectoparasiticide, comprising applying a quantity of a cleansing composition according to any one of Embodiments 42 to 58 directly to the skin or hair; wherein an effective amount of the ectoparasiticide remains on the skin or hair after applying the cleansing composition.

Embodiment 60

A method of treating the skin or hair on a dog containing an effective amount of an ectoparasiticide previously applied to the skin or hair, comprising applying a quantity of a cleansing composition according to any one of Embodiments 42 to 58 directly to the skin or hair, wherein the treatment does not result in reducing the efficacy of the ectoparasiticide against adult fleas (*C. felis*) or adult ticks (*R. sanguineus*) below 90% efficacy for at least a month after application of the ectoparasiticide.

Embodiment 61

A method of treating keratin material containing an effective amount of an ectoparasiticides on a pet wherein the treating is without the use of a water supply, comprising the steps:
(a) applying a quantity of a cleansing composition according to any one of Embodiments 42 to 58 directly to the dry keratin material sufficient to produce a wet keratin material; and
(b) drying the wet keratin material of step (a) to produce a final dry keratin material; wherein an effective amount of the ectoparasiticides remains on said keratin material after drying.

Embodiment 62

A method according to any one of Embodiments 59 to 61 wherein the treating is conditioning, strengthening, cleansing or moisturizing.

Embodiment 63

A method according to any one of Embodiments 59 to 61 wherein the treating imparts a shine onto the keratin material, skin or hair.

Embodiment 64

A method according to any one of Embodiments 59 to 61 wherein the treating provides a sebum reduction benefit to the keratin material, skin or hair.

Embodiment 65

A method according to any one of Embodiments 59 to 61 wherein the treating provides smoothness or softness to the keratin material, skin or hair.

Embodiment 66

A method according to any one of Embodiments 59 to 61 wherein the treating improving the appearance of the keratin material, skin or hair.

Embodiment 67

A method according to any one of Embodiments 59 to 61 wherein the treating provides a freshness, cleanliness and pleasurableness value onto the keratin material, which is greater than 50 on a scale of from 1 to 100.

Embodiment 68

A method according to any one of Embodiments 59 to 61 wherein the treating provides a deodorizing effect onto the keratin material, skin or hair.

Embodiment 69

A method according to Embodiment 68 wherein the deodorizing effect has a value which is less than 2 on a scale of from 1 to 5.

Embodiment 70

A method according to any one of Embodiments 59 to 69 wherein the ectoparasiticide is selected from the group consisting of metaflumizone, amitraz, methoprene, permethrin, pyriproxyfen, moxidectin, demiditraz, fipronil, fluralaner, afoxalaner, sarolaner, lotilaner, pyriprole, dinotefuran and imidacloprid.

Embodiment 71

A method according to any one of Embodiments 59 to 70 wherein the ectoparasiticide is fipronil.

Embodiment 72

A method according to any one of Embodiments 59 to 70 wherein the ectoparasiticide is ectoparasiticide products shown in the following table:

| Ectoparasiticide Product | Ingredient | CAS No | Content % |
|---|---|---|---|
| Frontline Plus (Merial) | Fipronil | 120068-37-3 | 10 |
| | Methoprene | 40596-69-8 | 9 |
| | Ethanol | 64-17-5 | 7.9 |
| | Non-Hazardous Ingredient | — | About 10 |
| | Glycol ether | — | to 100 |
| Frontline (Merial) | Fipronil | 120068-37-3 | 10 |
| | Ethanol | 64-17-5 | 10 |
| | Non-Hazardous Ingredient | | 80 |
| Vectra ® 3D (Ceva) | Permethrin | 52645-53-1 | 35-37 |
| | Dinotefuran: (1-Methyl-2-nitro-3-[(3-tetrahydrofuryl)methyl]guanidine) | 165252-70-0 | 4.7-5.2 |
| | Pyriproxyfen (2-[1-Methyl-2-(4-phenoxyphenoxy)ethoxy]pyridine) | 95737-68-1 | 0.4-0.48 |
| Advantage multi for Cats or Dogs (Bayer) | Moxidectin | 113507-06-5 | 0.8645 |
| | Imidacloprid | 138261-41-3 | 9.11 |
| | Alcohol | — | 60-100 |
| | Carbonate Derivative | — | 10-30 |
| K9 Advantix (Bayer) | Permethrin | 52645-53-1 | 40.015 |
| | Imidacloprid | 138261-41-3 | 8.803 |
| | Pyriproxyfen | 95737-68-1 | 0.44 |
| | Amine Derivative | — | 30-60 |
| SentryPro (Sergeants) | Permethrin | 52645-53-1 | 0.1-1 |
| | Piperonyl butoxide | 51-03-6 | 0.1-1 |
| | Pyriproxyfen | 95737-68-1 | 0-0.1 |

-continued

| Ectoparasiticide Product | Ingredient | CAS No | Content % |
|---|---|---|---|
| Zodiac (Wellmark) | Piperonyl Butoxide: 5-[2-(2-butoxyethoxy) ethoxymethyl]-6-propyl-1,3-benzodioxole | 51-03-6 | 0.50 |
| | Pyrethrins | 8003-34-7 | 0.05 |
| | Inert ingredients (non-hazardous) | | 99.45 |

Embodiment 73

A method according to any one of Embodiments 59 to 72 wherein the effective amount of the ectoparasiticide remains on the skin or hair for about a month.

Embodiment 74

A method according to any one of Embodiments 59 to 73 wherein no ectoparasiticide is applied to the skin or hair after applying the cleansing composition.

Embodiment 75

A method according to any one of Embodiments 59 to 74 wherein the treatment does not result in reducing the efficacy of the ectoparasiticide against adult fleas (C. felis) or adult ticks (R. sanguineus) below 90% efficacy for at least two months.

Embodiment 76

A method according to any one of Embodiments 59 to 75 wherein no ectoparasiticide is reapplied to the, keratin material, skin or hair during the treatment.

Embodiment 77

A method according to any one of Embodiments 59 to 76 wherein the cleansing composition is a liquid or spray and is applied topically.

Embodiment 78

A method according to any one of Embodiments 59 to 77 wherein the quantity of cleansing composition applied is about 0.2 g to about 0.3 g of cleansing composition per 1 Kg of dog.

Embodiment 79

A method according to any one of Embodiments 59 to 78 wherein the cleansing composition is applied about daily or about weekly.

Embodiment 80

A method according to any one of Embodiments 59 to 79 wherein the treatment does not include rinsing off the cleansing composition with water from the skin or hair.

Embodiment 81

A method according to any one of Embodiments 59 to 80 wherein the skin or hair is dried after applying the cleansing composition, by means of a evaporation or a towel, which removes most of the cosmetically acceptable carrier.

Embodiment 82

A kit for treating the skin or hair on a dog comprising:
a) a first container containing a cleansing composition according to any one of Embodiments 42 to 58;
b) a second container containing an ectoparasiticide; and
c) instructions for use of said kit, wherein said instructions do not direct rinsing the cleansing composition from the skin or hair.

Embodiment 83

A kit according to Embodiment 82, wherein following said instructions results in no effective amount of ectoparasiticides is removed from the skin or hair.

Embodiment 84

An embodiment according to the invention wherein the cleansing composition is a non-rinse shampoo.

The compositions of the present disclosure can comprise at least one additional ingredient conventionally used in the field, such as antioxidants, essential oils, preservatives, cosmetic or dermatological active principles, such as moisturizers (glycerol), vitamins, essential fatty acids, lipophilic sunscreens, fat-soluble polymers, in particular hydrocarbonaceous polymers such as polyalkylenes, gelling agents for the aqueous phase, gelling agents for the fatty phase, fragrances, surfactants, and mixtures thereof.

Examples of such essential oils or their constituents include, but are not limited to, eucalyptus oil, geranium oil, lemongrass oil, petitgrain oil, rosemary oil, thyme oil (white and red), lavender oil, tea tree oil, *Tagete minuta* oil, lovage oil, *Lippia javanica* oil, lemon oil, orange oil, grapefruit oil, oil of bergamot, galbanun oil, synthetic types of organic fragrances as described in U.S. Pat. Nos. 4,411,829 and 4,314,915, acetophenone, allyl caprate, α-amylcinnamic aldehyde, amyl salicylate, trans-anethole, anisaldehyde, benzyl alcohol, benzyl acetate, benzyl propionate, borneol, β-caryophyllene, caryophyllene, cinnamyl acetate, cinnamaldehyde, cinnamic alcohol, cinnamyl alcohol, carvacrol, carveol, citral, citronellal, citronellol, cumin aldehyde, cyclamen aldehyde, decanol, dimethyl salicylate, ethyl butyrate, ethyl caprate, ethyl cinnamate, eucalyptol (cineole), eugenol, iso-eugenol, galaxolide, geranial, geraniol, germacrene D, guaiacol, hexenol, α-hexylcinnamic aldehyde, hydroxycitrolnellal, ionone, ipsdienone, isopropenyl acetophenone, linalol, linalyl acetate, d-limonene, menthol, p-methylacetophenone, methyl anthranilate, methyl dihydrojasmonate, methyl eugenol, methyl ionone, methyl salicylate, neral, α-phellandrene, pennyroyal oil, perillaldehyde, 1- or 2-phenyl ethyl alcohol, 1- or 2-phenyl ethyl propionate, piperonal, piperitenone, piperonyl acetate, piperonyl alcohol, o-isopropenyl anisole, D-pulegone, terpinen-4-ol, terpinyl acetate, 4-tert-butylcyclohexyl acetate, α-terpineol, thymol, trans-tagetenone, myrcenone, linalool, carvone, ipsenone, α-phellandrene, piperitenone, gamma-undecalactone, undecenal, vanillin, and ethyl vanillin.

Essential oils can be pure single compounds, for example, wintergreen oil (methyl salicylate). However, other essential oils are mixtures of compounds, for example turpentine oil (pinene and dipentene); bitter almond oil (benzaldehyde and hydrocyanic acid); lavender oil (including borneol, fenchol, linalol, α-terpineol, terpinen-4-ol, geranyl acetate, linanyl acetate, terpenyl acetate, camphor, 1,8-cineole, camphene, limonene), pinene (3-caryophyllene, farnascene and coumarin); and tea tree oil (including linalol, α-terpineol, terpinen-4-ol, 1,8-cineole, limonene, myrcene, phellandrene, pinene, α-terpene, -caryophyllene and sabinene). Other essential oils, their chemistry and plant families are known in the art. See, for example, S. Price, Aromatherapy Workbook—Understanding Essential Oils from Plant to Bottle, (HarperCollins Publishers, 1993; J. Rose, The Aromatherapy Book—Applications & Inhalations (North Atlantic Books, 1992); and The Merck Index (12th Ed. 1996), each of which is incorporated herein by reference.

When the essential oil is a mixture of compounds, the present invention encompasses each of the constituent compounds of the essential oil. The present invention also encompasses variants or mimics of such compounds that share one or more of their characteristics or functions.

As these plant essential oil compounds are known and used for other uses, they may be routinely prepared by a skilled artisan by employing known methods. Exemplary methods for deriving an essential oil include steam distillation, pressing fruit rinds, solvent extraction, macerating the flowers and leaves in fat and treating the fat with solvent, enfleurage and synthetically. See, e.g., Price, Aromatherapy Workbook—Understanding Essential Oils from Plant to Bottle (HarperCollins Publishers, 1993, the entire disclosure of which is incorporated by reference herein).

The composition according to the invention can be present in the form of a liquid, semi-liquid, cream, foam, spray, lotion, gel or powder and is intended for topical application to the skin and/or hair or an animal Examples of compositions according to the invention include, but are not limited to, shampoo, conditioning shampoo, skin cleansers, skin moisturizer, and the like, and can be left on the animal after application.

For the embodiment as a pump spray, the composition is present in a non-aerosol container having a spraying apparatus. For the embodiment as an aerosol spray the composition additionally comprise at least one propellant, and are packaged in a pressurized-gas container ("aerosol container") having a spraying apparatus.

When the cosmetically acceptable carrier is a liquid carrier, the liquid carrier may comprise water and mixtures of water and at least one cosmetically acceptable solvent chosen from ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, isododecane, polybutene, hydrogenated poly isobutene, hydrogenated polydecene, polydecene, squalene, petrolatum and isoparaffins; and mixtures, thereof. Such liquid carriers, optionally in combination with other cosmetically acceptable excipients, provide the compositions of the present invention in the form of lotions, emulsions, gels, non-aerosol sprays or even in the form of pressurized compositions for aerosols, sprays or foams.

The liquid carrier can be present in the compositions of the present invention in the amount of about 95%, 90%, 80%, 70%, 60%, 50%, 40%, 30%, 20%, 10%, 5% by weight or less, based on the total weight of the composition.

A composition of the inventon may also contain one or more surfactants, for example different types of surfactants or more than one surfactant of the same type (ionic or nonionic). These surfactants are selected from anionic, non-ionic, cationic and amphoteric/zwitterionic surfactants, and mixtures thereof.

Typical examples of anionic surfactants include alkali metal sulforicinates, sulfonated glyceryl esters of fatty acids such as sulfonated monoglycerides of coconut oil acids, salts of sulfonated monovalent alcohol esters such as sodium oleylisethianate, metal soaps of fatty acids, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanolamine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulphuric esters of polyoxyethylene alkyl ethers.

Typical examples of cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines such as undecylimidazoline, fatty amides derived from disubstituted amines such as oleylanlinodiethylamine, derivatives of ethylene diamine, quaternaryammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides such as octyltrimethylammonium hydroxide, dodecyltrimethylanunonium hydroxide, or hexadecyltrimethylanunonium hydroxide, dialkyldimethylammonium hydroxides such as octyldimethylammonium hydroxide, decyldimethylammonium hydroxide, didodecyldimethylammonium hydroxide, dioctadecyldimethylammonium hydroxide, tallow trimethylammonium hydroxide, trimethylammonium hydroxide, methylpolyoxyethylene cocoammonium chloride, and dipalmityl hydroxyethylammonium methosulfate, amide derivatives of amino alcohols such as beta-hydroxylethylstearylamide, and amine salts of long chain fatty acids.

Typical examples of nonionic surfactant components include, for example, long-chain fatty acid mono- and dialkanolamides, such as coco fatty acid monoethanolamide and myristic fattyacid monoethanolamide, which can also be used as foam enhancers; sorbitan esters, such as polyethylene glycol sorbitan stearic acid ester, fatty acid poly glycol esters or poly-condensates of ethyleneoxide and propyleneoxide, as they are on the market, for example, under the trade name "Pluronics"; fatty alcohol ethoxylates; aminoxides such as lauryl dimethyl aminoxide, di(hydroxyethyl) or (hydroxypropyl) aminoxides, aminoxides with ethyleneoxide and/or propyleneoxide groups in the alkyl chain such aminoxides are on the market, for example, under the trade names "Ammonyx", "Aromox" or "Genaminox"; alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e. g., "Laureth-16" and "Laureth-2" wherein the average degree of ethoxylation thereby ranges between about 2.5 and about 25, for example about 10 and about 20; polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters; condensates of ethylene oxide with a long chain (fatty) alcohol or (fatty) acid, condensates of ethylene oxide with an amine or an amide, condensation products of ethylene and propylene oxides, fatty acid alkylol amide and fatty amine oxides; polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol and alkyl-polysaccharides.

Typical examples of amphoteric or zwitterionic surfactants include, for example, aliphatic secondary or tertiary amine derivatives in which the aliphatic radical is a linear or branched chain containing 8 to 22 carbon atoms and containing-at least one water-soluble anionic group (for example carboxylate, sulphonate, sulphate, phosphate or phosphonate); for example ($C_8$-$C_{20}$)alkylbetaines, sulphobetaines, ($C_8$-$C_{20}$)alkylamido($C_1$-$C_6$)alkylbetaines, fatty acid amidoalkyl betaines and sulfobetaines, for example, lauryl hydroxysulfobetaine; long-chain alkyl amino acids, such as cocoaminoacetate, cocoaminopropionate, sodium cocoamphoacetate and sodium cocoamphopropionate.

Other surfactants which can be used include those disclosed "Cosmetology—Theory and Practice', 2005, Verlag Fur Chemische Industrie, Augsburg Germany; "International Cosmetic Ingredient Dictionary & Handbook", 15th Edition, The Personal Care Products Council; "Applications of Personal Care Detergent Formulations", Louis Ho Tan Tai et al., "Handbook of Detergents", Part E: Applications CRC Press 2009; "Body-Cleansing Technology S. Abbas, Handbook of Detergents, Part E: Applications CRC Press 2009; and Applications of Surfactants in Shampoos, Handbook of Detergents, Part E: Applications CRC Press 2009. Incorporated herein by reference.

Other types of surfactants may be added to compositions of the invention are added to shampoos to improve the foaming characteristics of the formulation. These materials, called alkanolamides, help increase the amount of foam and the size of the bubbles.

In the compositions of the invention the concentration of the surfactant generally ranges from about 3 to about 50% by weight, for example from about 3 to about 20% by weight, and about 0.5 to about 5% by weight based on the total weight of the composition.

Another embodiment of the invention is a composition of the invention which is essentially free of surfactant.

A foam enhancer is an agent which increases the amount of foam available from a system at a constant molar concentration of surfactant, in contrast to a foam stabilizer which delays the collapse of a foam. Foam building is provided by adding to the aqueous media, a foam boosting effective amount of a foam enhancer. Typical examples of foam enhancer include, for example, fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) $C_{12}$-$_{15}$ alkoxypropylamine oxide. Additional foam enhancer are those disclosed in Hart, J. R. and Degeorge, M. T. (1980) J. Soc. Cosmet. Chem., 31, 223-236; Fox, C, Formulation of shampoos, Cosmet. Toiletries, 1988, 103(3), 25-58; and Rieger, M., Surfactants in shampoos, Cosmet. Toiletries, 1988, 103(3), 59-72.

The foam enhancer is present in the shampoo compositions of this invention in an amount from about 0.5 to about 15 wt %, for example about 1 to about 10 wt % based on the total weight of the composition.

When the compositions according to the invention are provided in the form of cream, they contain one or more emulsifying agents, for example different types of emulsifying agents or more than one s emulsifying agents of the same type (ionic or nonionic). These emulsifying agents are selected from anionic, or nonionic emulsifying agents, and mixtures thereof.

Typical examples of nonionic emulsifying agents comprise principally mixtures of oils and/or fatty alcohols or polyethoxylated alcohols such as polyethoxylated stearyl or cetylstearyl alcohols. Typical examples of anionic emulsifying agents are essentially soaps. Other emulsifiers that can be used according to the invention are those disclosed in U.S. Pat. No. 8,894,983. In these shampoo compositions, the concentration of the emulsifying agent generally ranges from about 0.5 to about 8 wt % of the composition.

When the compositions according to the invention are provided in the form of thickened lotions or gels, they contain thickening agents in the presence or not of solvents.

Typical examples of thickening agents include, for example, sodium alginate, gum arabic, xanthane gum, or cellulose derivatives such as as methyl cellulose, hydroxymethyl cellulose, hydroxyethyl cellulose, hydroxyl propyl cellulose, hydroxypropylmethyl cellulose or carboxymethyl cellulose.

The concentration of the thickening agent can range from about 0.1 to about 10% by weight, for example from about 0.2 to about 2% by weight based on the total weight of the composition.

A composition of the inventon may also contain a conditioning agent for providing a conditioning benefit to the skin, hair and other parts of the body with keratin-containing tissue. Hair conditioning agents are hair care products that alter the texture and/or appearance of animal hair to facilitate combing of the hair and/or to improve the shine and/or softness of the hair, or add sensory feel on the skin.

Typical examples of conditioning agent include, for example, a water soluble conditioning agent; an oil soluble conditioning agent; a conditioning emulsion; or any combination or permutation of the three.

Non-limiting examples of useful conditioning agents include those selected from the group consisting of amino acids, petrolatum, fatty acids, esters of fatty acids, fatty alcohols, ethoxylated alcohols, polyol polyesters, glycerine, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, poly olefinic glycols, polyolefinic monoester, polyolefinic polyesters, cholesterols, cholesterol esters, triglycerides and mixtures thereof.

More particularly, the conditioning agent may be selected from the group consisting of paraffin, mineral oil, petrolatum, stearyl alcohol, cetyl alcohol, cetearyl alcohol, behenyl alcohol, $C_{10}$-$C_{30}$ polyesters of sucrose, stearic acid, palmitic acid, behenic acid, oleic acid, linoleic acid, myristic acid, lauric acid, ricinoleic acid, steareth-1-100, cetereath 1-100, cholesterols, cholesterol esters, glyceryl tribehenate, glyceryl dipalmitate, glyceryl monostearate, trihydroxystearin, ozokerite wax, jojoba wax, lanolin wax, ethylene glycol distearate, candelilla wax, carnauba wax, beeswax, and silicone waxes. The conditioner can for example be an organopolysiloxane as described for example in EP-A-432951, EP-A-798332, U.S. Pat. No. 6,013,682, EP-A-1263840 and EP-A-1054032.

Additional conditioning agents, other than the silicone conditioning agents, may be added to the composition, for example cationic conditioning agents such as quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats including Non-limiting examples of cationic polymers and ampholytic polymers include hexadimethrine chloride, polyquaternium-4, polyquaternium-6, poly quaternium-7, polyquaternium-10, polyquaternium-11, polyquaternium-16, polyquaternium-22, polyquaternium-32, polyquaternium-39, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, and polyquaternium-94. The above cationic organic polymers and others are described in more details in U.S. Pat. No. 4,240,450 which is hereby incorporated by reference to further describe the cationic organic polymers. Other categories of conditioners such as cationic surfactants such as cetyl trimethylammonium chloride, cetyl trimethyl ammonium bromide, and stearyltrimethyl ammonium chloride, may also be employed in the compositions as a cationic conditioning agent.

Further conditioning agents may include common amino acids, and salts thereof, such as Alanine, Arginine, Asparagine, Aspartic Acid, Cysteine, Glutamic Acid, Glutamine, Glycine, Histidine, Isoleucine, Leucine, Lysine, Methionine, Phenylalanine, Proline, Serine, Threonine, Tryptophan, Tyrosine and Valine. The amino acid salts include Arginine HCl, Calcium Aspartate, Calcium Glycinate, Cysteine HCl, Dipotassium Aspartate, Histidine HCl, Lysine HCl, Magnesium Aspartate, Magnesium Glycinate, Potassium Aspartate, Sodium Aspartate, Sodium Glutamate and Sodium Glycinate.

Further conditioning agents may be nonionic polymers, for example alcohol and/or water-soluble vinyl pyrrolidone polymers, such as a vinyl pyrrolidone homopolymers or copolymers. Useful vinyl pyrrolidone polymers are, e. g. those known by the trade name "Luviskol", for example, the homopolymers "Luviskol K 30, K 60 and K90", as well as the water- or alcohol-soluble copolymers from vinyl pyrrolidone and vinyl acetate, distributed by BASF AG under the trade name "Luviskol VA 55 respectively VA 64". Further possible nonionic polymers are vinyl pyrrolidone/vinyl acetate/vinyl propionate copolymers such as "Luviskol VAP 343", vinyl pyrrolidone/(meth)acrylic acid ester copolymers, as well as chitosan derivatives. Amphoteric polymers are found to be useful in conditioning composition of any type of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomer"; copolymers from methacryloylethyl betaine and alkyl-methacrylates of the type "Yukaformer", e. g., the butyl methacrylate copolymer "Yukaformer Am75"; copolymers from monomers containing carboxyl groups and sulfonic groups, e. g., (meth)acrylic acid and itaconic acid, with monomers such as mono or dialkyl amino alkyl(meth)acrylates or mono- or dialkylaminoalkyl (meth)acrylamides containing basic groups, in particular amino groups; copolymers from N-octyl acrylamide, methyl methacrylate, hydroxypropyl methacrylate, N-tert-butyl aminoethyl methacrylate and acrylic acid, as well as the copolymers known from U.S. Pat. No. 3,927,199, are applicable. Other Conditioning agents include those listed in the International Cosmetic Ingredient Dictionary and Handbook, 15th Edition, 2014.

The concentration of the conditioning agent can range from about 0.1 to about 15% by weight, for example about 5 to about 10% by weight based on the total weight of the composition.

The composition of the invention may also contain preservatives such as ethanol, parabens, butylated hydroxytoluene (BHT), potassium sorbate, butylated hydroxyanisole (BHA), chlorphenesin phenoxyethanol, ethylhexylglycerin or the like. Additional preservatives that can be used are disclosed in New Alternatives to Paraben Based Preservative Blends, Weber, K, Cosmetic and Toiletries Magazine, 120, 1, p 57-62 (January 2005).

Preservatives suitable within the scope of the invention are present in an amount from about 0.01 to about 5% by weight, based on the total weight of the composition.

The composition of the invention may also contain one or more modifiers to modify specific characteristics of the composition, for example a pearlizer, a sequestering agent, a viscosity modifier, and a pH adjusting agent.

Pearlizer give the composition a pearly look, such as glycol distearate, diethylene glycol monostearate, monoethylene glycol onostearateor pearl concentrates.

Sequestering agents offset the dulling effects of hard water, such as tetrasodium EDTA, sodium carbonate, sodium sesquicarbonate or sodium citrate.

Viscosity modifiers adjust the viscosity and/or the stability of the composition. Some useful and popular viscosity modifiers are for example inorganic salts such as magnesium nitrate, trimagnesium phosphate, calcium chloride, sodium carbonate, sodium chloride, sodium aluminum sulfate, di sodium phosphate, sodium polymetaphosphate, sodium magnesium succinate, sodium sulfate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, annnonium phosphate, annnonium sulfate, calcium acetate, calcium nitrate, calcium phosphate, calcium sulfate, ferric sulfate, magnesium chloride, magnesium sulfate, alkyl ether sulfate, mixtures thereof, and the like, or polymers such as sodium laureth sulfate (SLS); sodium lauryl ether sulfate (SLES); sodium lauryl sulfoocetate; sodium lauryl sulfoacetate and disodium laureth sulfosuccinate; Sodium methyl 2-sulfolaurate and disodium 2-sulfolaurate and sodium lauryl sulfoacetate.

In the liquid compositions of the invention, the concentration of the viscosity modifier generally ranges from about 0.1% to about 10%, from about 0.3% to about 5.0%, or from 0.5% to 3% by weight based on the total weight of the composition.

pH adjusting agent adjust the pH of composition in solution. pH adjusters include water soluble bases or acids such as carboxylic acid, a mineral acid or their mixture. The pH adjusting agents include but are not limited to mineral acids such as hydrochloric acid, sulphuric acid, and phosphoric acid, carboxylic acid such as citric acid and lactic acid, glycolic acid, hydroxyacrylic acid, glyceric acid, malic acid, tartaric acid, malonic acid, succinic acid, glutaric acid, adipic acid, glucuronic acid, maleic acid, fumaric acid, phtalic acid and acetic acid. Suitable bases include sodium hydroxide. pH adjusting agent preferably adjust the pH of the composition within the range of about 4 to about 9 and more preferably within the range of about 5 to about 7.

The liquid compositions according to the invention can exhibit a viscosity of from about 1,000 centipoise (cP) to about 1,000,000 cP, about 1,500 cP to about 1,000,000 cP, from about 5,000 cP to about 1,000,000 cP, from about 6,000 cP to about 1,000,000 cP, or from about 8,000 cP to about 1,000,000 cP, at about 25° C. as measured by the method described in US Patent Number US 20140121268. The viscosity of the compositions can be adjusted with known viscosity modifiers.

It should be noted that in the case that a composition are delivered in the form of a foam from a pump-foamer and/or aerosol can, those compositions should not be thickened and have a viscosity value not more than about 500 cP, for example about 250 cP measured as mentioned above at room temperature.

It should be noted that in the case that a composition are delivered in the form of a atomized spray from a pump dispenser, those compositions should not be thickened and have a viscosity value not more about 40 cP, for example less than about 30 cP.

A shampoo composition of the inventon may also contain an anti-dandruff agent for example pyridinethione salts such as zinc pyrithione, selenium compounds such as selenium disulfide, salicylic acid, ketoconazole, climbazole, octopirox, and piroctone olamine.

The anti-dandruff may be present in the composition disclosed herein in an amount ranging from about 0.001 to about 10% by weight, for example, from about 0.1 to about 5% by weight, or from about 0.2 to about 2% by weight based on the total weight of the composition.

A composition of the inventon may also contain vitamins for example lipid-soluble vitamins that have utility in personal care formulations include retinal (vitamin A), ergocalciferol (vitamin D2), cholecalciferol (vitamin D3), phytonadione (vitamin K1), and tocopherol (vitamin E). Water-soluble vitamins that have utility in personal care formulations include ascorbic acid (vitamin C), thiamin (vitamin B1) niacin (nicotinic acid), niacinamide (vitamin B3), riboflavin (vitamin B2), pautothenic acid (vitamin B5), biotin, folic acid, pyridoxine (vitamin B6), cyauocobalamin (vitamin Bu) and derivatives thereof. Derivatives of retinal include retinyl palmitate (vitamin A palmitate), retinyl acetate (vitamin A acetate), retinyl linoleate (vitamin A linoleate), and retinyl propionate (vitaulin A propionate). Derivatives of tocopherol include tocopheryl acetate (vitamin E acetate), tocopheryl linoleate (vitamin E linoleate), tocopheryl succinate (vitamin E succinate), tocophereth-5, tocophereth-10, tocophereth-12, tocophereth-18, tocophereth-50 (ethoxylated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin Ederivatives), and sodium tocopheryl phosphate. Derivatives of ascorbic acid (Vitamin C) such as ascorbyl palmitate, ascorbyl dipalmitate, ascorbyl glucoside, ascorbyl tetraisopalmitate, and tetrahexadecyl ascorbate.

The vitamin may be present in an amount ranging from about 0.1 to about 5% by weight, based on the total weight of the composition.

A composition of the inventon may also contain proteins for example those extracted from wheat, soy, rice, corn, keratin, elastin, milk or silk. Most are in the hydrolyzed form and they can also be quaternised to provide better performance.

A composition of the inventon may also contain a moisturizing agent which include, but are not limited to: glycols, sugars, fatty alcohols, fatty alcohol derivatives and the like. Suitable glycols are in monomeric or polymeric form and include polyethylene and polypropylene glycols such as PEG4-200, which are polyethylene glycols having from 4 to 200 repeating ethylene oxide units; as well as C1-6 alkylene glycols such as propylene glycol, ethylene glycol, polyethylene glycol, caprylyl glycol, polypropylene glycol, butylene glycol, pentylene glycol, hexylene glycol, isoprene glycol, and the like. Suitable sugars, some of which are also polyhydric alcohols, are also suitable humectants. Examples of such sugars include, but are not limited to glucose, fructose, honey, hydrogenated honey, inositol, maltose, mannitol, maltitol, sorbitol, sucrose, xylitol, xylose, and the like.

Examples of fatty alcohols as moisturizing agents are straight-chain-saturated or unsaturated alcohols with chain lengths between $C_6$ and $C_{24}$. Examples of fatty alcohol derivatives include, but are not limited to butyl stearate, caprylic/caprictriglyceride, coco caprylate/caprate, cetearyl isononanoate, cetyl palmitate, decyl oleate, hexyldecyl stearate, isopropyl myristate, isopropyl palmitate, myreth-3-myristate, myristyl myristate, octyl stearate, octyldodecyl stearate, oleyl erucate, PEG-7-glycerylcocoate, propylene glycol isostearate, propylene glycol dicaprylate/dicaprate, propylene glycol dipelargonate, propylene glycol dicaprylate/dicaprate, and shea butter.

The moisturizing agents may be present in the composition in an amount ranging from about 0.5 to about 2.0% by weight, for example from about 0.8 to about 1.0% by weight, based on the weight of the composition.

A composition of the inventon may also contain a fragrance for example fragrant odoriferous substance or a mixture of fragrant odoriferous substances including natural substances obtained by extraction of flowers, herbs, leaves, roots, barks, wood, blossoms or plants; artificial substances including mixtures of different natural oils or oil constituents; and synthetically produced substances. A list of suitable fragrances is provided in U.S. Pat. Nos. 4,534,891, 5,112,688 and 5,145,842. Another source of suitable fragrances is found "Perfumes, Cosmetics, and Soaps" edited by W. A. Poucher; Springer; 10th ed. (May 31, 2000).

A composition of the inventon may also contain a solubilizer, in particular cleansing compositions, especially when oily substances are chosen as conditioning agents and fragrance with highly lipophilic properties. Typical solubilizers may be polyethylene glycols, isopropyl palmitate, isopropyl myristate, mineral oils, silicone oils and the like.

The solubilizers may be present in the composition in an amount ranging from about 0.01 to about 2% by weight, for example from about 0.1 to about 1% by weight, based on the total weight of the composition A composition of the inventon may also contain at least one plant extract or a mixture thereof. The extracts from green tea, oak bark, nettle, witch hazel, hops, henna, chamomile, burdock root, horsetail, hawthorn, linden blossoms, almond, *Aloe vera*, pine needles, horse chestnut, sandalwood, juniper, coconut, mango, apricot, lemon, wheat, kiwi fruit, melon, orange, grapefruit, salvia, rosemary, birch, mallow, lady's smock, wild thyme, yarrow, thyme, lemon balm, restharrow, coltsfoot, hibiscus, meristem, ginseng, ginger root, *Sarothamnus scoparius* (common broom or scotch broom), *Juglans regia* (walnut), *Krameria triandra*, or *Plukenetia volubilis* (sacha inchi). The leaves, the stems and the roots of the plant may be used either singly or in combination as raw materials for the extract; or ingredients which are extracted separately from the leaves, the stems and the roots may be used in combination as required.

The plant extract may be present in the composition in an amount ranging from about 0.001 to 5% by weight, for example 0.01 to 1.0% by weight based on the total weight of the composition, calculated as a residue obtained after distillation of extraction solvent.

Desirably, only ingredients which are not irritating to the eye are used in the compositions of the invention.

Other examples of cosmetically acceptable excipients and examples methods of formulating the compositions of the invention are found in Knowlton, John and Steven Pearce. The Handbook of Cosmetic Science and Technology. Elsevier Science Publishers, 1993; Umbach, Wilfried. Cosmetics and Toiletries Development, Production, and Use. Ellis Horwood, 1991; Kintish, Lisa. "Shampoos Get Specific." Soap/Cosmetic/Chemical Specialties, October 1995, pp. 20-30; Cosmetics and Dermatologic Problems and Solutions, Third Edition (2011), By Zoe Diana Draelos; and Formulas, Ingredients and Production of Cosmetics: Technology of Skin- and Hair-Care Products in Japan, by Hiroshi Iwata, and Kunio Shimada, 2013th Edition, Springer.

Suitable spray containers that may be used to apply the liquid composition of the invention are well known in the art and include conventional, non-aerosol pump sprays i.e., "atomisers", aerosol containers or cans having a propellant, as described above, and also pump aerosol containers utilizing compressed air as the propellant.

The composition of the invention may also include a cosmetically acceptable excipient.

A composition according to the invention which does not contain any or all of the following parabens, isothiazolinone, quaternium-15, imidazolidinylurea (Germall 115), diazolidinyl urea (Germall II), DMDM Hydantoin (Glydant), 2-bromo-2-nitropropane-1,3-diol (Bronopol), tris (hydroxymethyl) nitromethane (Tris Nitro), hydroxymethylglycinate (Suttocide A), octamethylcyclotetrasiloxane, decamethylcyclopentasiloxane, phenoxyethanol, BHA, BHT, mineral oil and cocamide diethanolamine.

The plant extract is obtained by extracting flowers, leaves, fruits, roots, stems and the like with solvent at ambient temperature or with heating according to any known extraction technique. The extraction solvents may be used either singly or in combination and include polar organic solvents and hydrophobic solvents. Examples of polar organic solvents include, for example, lower alcohols ($C_{1-6}$) such as methanol, ethanol and the like, $C_{2-6}$ alkylene glycols such as propylene glycol, 1,3-butylene glycol and glycerin, and water. Examples of hydrophobic solvents include, for example, chloroform and diethyl ether. These solvents may be used singly or in combination.

The processing of shampoo compositions in general has been presented by several Patents and publications, among which are U.S. Pat. Nos. 3,476,489, 3,152,046, 2,826,551 A British Patent 1,051,268, Canadian Patent 1213831, Mottram F J, Lees C E. Hair shampoos. In Butler H (ed.). Poucher9s perfumes, cosmetics and soaps, 10th edition. Dordrecht. Kluwer Academic Publishers, 2000: pp. 289-306.

The efficacy of the ectoparasiticide can be measured by known methods for example by the methods disclosed in Rosentel, Jr., J et al. (U.S. Pat. No. 9,173,403) and Jeannin (U.S. Pat. No. 6,083,519).

The examples are presented to further illustrate and explain the present invention and should not be taken as limiting in any regard. Unless otherwise indicated in the examples and elsewhere in the specification and claims, all parts and percentages are by weight. Temperatures are in degrees Centigrade.

EXAMPLES

Example 1: "Freshness", "Cleanliness", "Pleasant Feeling" and Deodorizing Effect of the Composition The composition shown in the examples are made using conventional methods known to a skilled person in the art:
A)—Pet Shampoo A:

| Ingredient | % |
|---|---|
| Deionized Water | 92.152% |
| Glycerin | 2.048% |
| Silsense DW-18 | 3.584% |
| Citral | 0.030% |
| γ-Nonalactone | 0.160% |
| Coconut Extract | 0.160% |
| Rosemary Extract | 0.120% |
| Aloe Vera Extract | 0.030% |
| Arnica Extract | 0.030% |
| Echinacea Extract | 0.030% |

| Ingredient | % |
| --- | --- |
| Horsetail Extract | 0.030% |
| Vitamin E | 0.030% |

The quality of pet's coat after application of Pet Shampoo A to the pet's coat is judged on the basis of "freshness" (or refreshing feeling), "cleanliness" (or cleanness, or clean feeling) and "pleasant feeling" (or agreeable feeling or "pleasurableness") according to a standardized evaluation method as explained in the present invention. The flavor or fragrance of the invention preferably meets the satisfaction criteria for "freshness", "cleanliness" and "pleasant feeling" mentioned above. The satisfaction criteria are expressed in terms of scores ranging from 0 to 100 points. Typically, the scores exceeding 50 points signify a satisfactory result.

The freshness, cleanliness and pleasant feeling of the pet's coat after application of Pet Shampoo A is evaluated as follows.

Pet Shampoo A was sprayed liberally all over the dog. The dogs were sprayed, holding the spray applicator at a distance of 15 cm to 23 cm (6" to 9") or 10 cm to 15 cm (4" to 6" for XS dogs) from the animal's skin. The shampoo was not sprayed in eyes or other orifices.

The amount of Pet Shampoo A applied, to each dog was from about 0.2 g to about 0.3 g/Kg of dog and outlined in the table below.

| Dog size | kg | lbs. | Spray Pumps |
| --- | --- | --- | --- |
| XS | <3.6 | <8 | 4 |
| S | 3.6 to 9.0 | 8 to 20 | 8 |
| M | 9.1 to 20.4 | 21 to 45 | 15 |
| L | 20.5 to 40.8 | 45 to 90 | 20 |
| XL | >40.8 | >90 | 30 |

A panel of 3 to 5 persons observe the pets coat and rate the results from zero to 100 points for three criteria, freshness, cleanliness and pleasant feeling. The average of the results for each criteria are then obtained. Rating standards are defined in Table 1 (freshness), Table 2 (cleanliness) and Table 3 (pleasant feeling).

TABLE 1

| Scores | Evaluation |
| --- | --- |
| 0 | No freshness |
| 25 | Little freshness |
| 50 | Partial freshness |
| 75 | Strong freshness |
| 100 | Very strong freshness |

TABLE 2

| Scores | Evaluation |
| --- | --- |
| 0 | No cleanliness |
| 25 | Little cleanliness |
| 50 | Partial cleanliness |
| 75 | Strong cleanliness |
| 100 | Very strong cleanliness |

TABLE 3

| Scores | Evaluation |
| --- | --- |
| 0 | No pleasant feeling |
| 25 | Little pleasant feeling |
| 50 | Partial pleasant feeling |
| 75 | Strong pleasant feeling |
| 100 | Very strong pleasant feeling |

The deodorizing effect of the composition on the pet's coat after application of the composition is evaluated as follows.

The deodorizing effect of the composition is evaluated by a panel of 3 to 5 persons. The results of the evaluation are rated into 5 levels of score. Rating standards are defined in Table 4

TABLE 4

| Scores | Malodor-smelling index |
| --- | --- |
| 0 | No malodor smelling |
| 1 | Hardly smelling |
| 2 | Weak but identifiable smelling |
| 3 | Easily identifiable smelling |
| 4 | Strong smelling |
| 5 | Very strong smelling |

Example 2

A)—Pet Shampoo A

| Ingredient | % |
| --- | --- |
| Deionized Water | 92.152% |
| Glycerin | 2.048% |
| Silsense DW-18 | 3.584% |
| Citral | 0.030% |
| γ-Nonalactone | 0.160% |
| Coconut Extract | 0.160% |
| Rosemary Extract | 0.120% |
| Aloe Vera Extract | 0.030% |
| Arnica Extract | 0.030% |
| Echinacea Extract | 0.030% |
| Horsetail Extract | 0.030% |
| Vitamin E | 0.030% |

The objective of the study was to identify any effect of the frequency of use of Pet Shampoo A on the efficacy of fipronil (Frontline® Plus) against adult *Ctenocephalides felts* (*C. felis*) fleas and adult *Rhipicephalus sanguineus* (*R. sanguineus*) ticks on dogs.

Twenty-four (24) healthy dogs weighing 15.2 kg to 23.8 kg on Day −1 were studied in this parallel group designed, randomised, single centre, blinded, positive controlled comparative study. On Day −1, the 24 dogs included were ranked within sex in descending order of individual pre-administration live flea counts and subsequently blocked into eight blocks of three dogs each and allocated to three groups.

Frontline® Plus was administered to the dogs at a dose of 1.34 mL/dog weighing 10 kg to ≤20 kg or 2.68 mL/dog weighing 20 kg to ≤40 kg. The Frontline® Plus dose was applied topically to each dog at two spots, one between the shoulder blades and one towards the neck. The Frontline® Plus was applied directly to the skin through parting the hair until the skin was visible. Time of administration of the Frontline® Plus was documented. Care was taken not to spill any product. Dogs were restrained for approximately one minute following administration, to prevent any possible run-off of the product. No spillages or run-off occurred.

The dogs were applied the Pet Shampoo as described below:

On Day −4, all dogs were shampooed with Purl Advanced hypoallergenic shampoo, rinsed thoroughly and dried, using a towel and blow dryer. The volume of shampoo applied and the time of shampooing were recorded.

Dogs in group 2 were shampooed daily with Pet Shampoo A from Day 2 to 28 (apart from Days 8, 15 and 22) and dogs in group 3 were shampooed with Pet Shampoo A on Days 3, 10, 17 and 24.

Shampoo was sprayed liberally all over the dog, daily or weekly, depending on the group. The dogs were sprayed, holding the spray applicator at a distance of 15 cm to 23 cm (6" to 9") or 10 cm to 15 cm (4" to 6" for XS dogs) from the animal's skin. Shampoo was not sprayed in eyes or other orifices.

TABLE A

Pet Shampoo A spray amount is outlined below.
The amount of Pet Shampoo A applied during daily, or at each 7-day intervals, to each dog was from about 0.2 g to about 0.3 g/Kg of dog.

| Dog size | kg | lbs. | Spray Pumps |
|---|---|---|---|
| XS | <3.6 | <8 | 4 |
| S | 3.6 to 9.0 | 8 to 20 | 8 |
| M | 9.1 to 20.4 | 21 to 45 | 15 |
| L | 20.5 to 40.8 | 45 to 90 | 20 |
| XL | >40.8 | >90 | 30 |

TABLE B

| Group | Treatment |
|---|---|
| Group 1 (positive control group) | Dogs (n = 8) were treated topically with Frontline ® Plus only, on Day 0 |
| Group 2: | Dogs (n = 8) were treated topically with Frontline ® Plus on Day 0 and daily with Pet Shampoo A from Day 2 to 28, except on Days 8, 15 and 22. |
| Group 3 | Dogs (n = 8) were treated topically with Frontline ® Plus on Day 0 and at 7-day intervals with Pet Shampoo A, from Day 3 to 24 (on Days 3, 10, 17 and 24). |

The primary criteria to determine any effect that Pet Shampoo A could have on the Frontline® Plus was the number of live adult ticks and adult fleas collected for the positive control group (group 1) and the Pet Shampoo A groups on the various days.

A clinical examination was performed on all dogs on Day −7 for enrolment and inclusion purposes and the animals were observed once daily for general health for the duration of the test.

Each dog was infested with 50 live *R. sanguineus* ticks (50% female:50% male) and 100 live *C. felis* fleas of mixed sex on Days 7, 14, 21 and 28. Any live Ticks and fleas were removed and counted as close as possible to the specified target times (48±2 hours after infestation). However, on Days 9, 16 and 23, the live tick and flea counting time was at 43 to 44 hours after flea infestation.

Based on arithmetic mean numbers of *R. sanguineus* ticks, no statistically significant differences were recorded between the positive control Group 1 (Frontline® Plus only) and Group 2 (Frontline® Plus in combination with the Pet Shampoo A administered daily) or Group 3 (Frontline® Plus in combination with the Pet Shampoo A administered weekly) to the dogs for up to one month following Frontline® Plus administration.

Based on arithmetic mean numbers of live *C. felis* fleas, no statistically significant differences were recorded between the positive control Group 1 (Frontline® Plus only) and Group 2 (Frontline® Plus in combination with the Pet Shampoo A administered daily) or Group 3 (Frontline® Plus in combination with the Pet Shampoo A administered weekly) to the dogs for up to one month following Frontline® Plus administration.

TABLE C

Arithmetic means of live ticks: *R. sanguineus*

| Day Group | Control Mean Group 1 | Mean Group 2 | p-value | Mean Group 3 | p-value |
|---|---|---|---|---|---|
| Day 9 | 0.1 | 0.1 | 1.0000 | 0.3 | 0.5320 |
| Day 16 | 0.0 | 0.1 | 0.2342 | 0.0 | 1.0000 |
| Day 23 | 0.4 | 0.3 | 0.6940 | 0.1 | 0.4340 |
| Day 30 | 1.8 | 0.1 | 0.5552 | 1.1 | 0.5552 |

TABLE D

Arithmetic means of fleas: *C. felis*

| Day Group | Control Mean Group 1 | Mean Group 2 | p-value | Mean Group 3 | p-value |
|---|---|---|---|---|---|
| Day 9 | 0.0 | 0.0 | | 0.0 | |
| Day 16 | 0.0 | 0.0 | | 0.0 | |
| Day 23 | 0.0 | 0.0 | | 0.0 | |
| Day 30 | 0.0 | 0.1 | 0.2342 | 0.0 | 1.0000 |

These results conclude that the use of Pet Shampoo A administered on a daily or weekly basis had no effect on the efficacy of fipronil (Frontline® Plus) against adult fleas (*C. felis*) or adult ticks (*R. sanguineus*) on dogs for up to one month after administration at doses of 1.34 mL/dog weighing 10 kg to ≤20 kg or 2.68 mL/dog weighing 20 kg to ≤40 kg.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is noted that the invention does not intend to encompass within the scope of the invention any previously disclosed composition, product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

What is claimed is:

1. A method of treating the skin or hair on a dog containing an effective amount of an ectoparasiticide for treating fleas or ticks that has been previously applied to the skin or hair of said dog, said method comprising applying directly to the skin or hair of said dog a quantity of a cleansing composition comprising:
   a) about 1-3% glycerin by weight of the total composition;
   b) about 2-4% silicone copolyol esters by weight of total composition; and
   c) water,
wherein the treatment does not result in reducing the efficacy of the ectoparasiticide against adult fleas or adult ticks below 90% efficacy for at least a month after application of said ectoparasiticide; and wherein said cleansing composition is essentially free of surfactant except for the silicone copolyol esters.

2. The method according to claim 1 wherein the cleansing composition does not contain an ectoparasiticide.

3. The method according to claim 1 wherein the the cleansing composition is applied daily or weekly.

4. The method according to claim 3 wherein the treatment does not result in reducing the efficacy of the ectoparasiticide against adult fleas or adult ticks below 90% efficacy for at least two months.

5. The method according to claim 1 wherein the treatment is conditioning, strengthening, cleansing or moisturizing.

6. The method according to claim 1 wherein the treatment is conditioning or cleansing.

7. The method according to claim 1 wherein the ectoparasiticide is selected from the group consisting of metaflumizone, amitraz, methoprene, permethrin, pyriproxyfen, moxidectin, demiditraz, fipronil, fluralaner, afoxalaner, sarolaner, lotilaner, pyriprole, dinotefuran and imidacloprid.

8. The method according to claim 1 wherein the ectoparasiticide is fipronil.

9. The method according to claim 1 wherein the quantity of cleansing composition applied is about 0.2 g to about 0.3 g of cleansing composition per 1 Kg of dog.

10. The method according to claim 1, wherein the treatment does not include rinsing off the cleansing composition with water from the skin or hair.

11. The method according to claim 1 wherein the cleansing composition is a liquid or spray and is applied topically.

12. The method according to claim 11 wherein the cleansing composition comprises:

| Ingredient | Amount (% by weight based on the total weight of the composition.) |
|---|---|
| water | about 92% |
| glycerin | about 2% |
| dimethicone PEG-7 isostearate (Silsense DW-18) | about 3% |
| Citral | about 0.1% |
| γ-Nonalactone | about 0.2% |
| Coconut Extract | about 0.2% |
| Rosemary Extract | about 0.1% |
| Aloe Vera Extract | about 0.1% |
| Arnica Extract | about 0.1% |
| Echinacea Extract | about 0.1% |
| Horsetail Extract | about 0.1% |
| Vitamin E | about 0.1% |

13. The method according to claim 1 wherein no extoparasiticide is reapplied to the skin or hair during treatment.

14. The method according to claim 1 wherein the cleansing composition is a non-rinse shampoo.

15. The method according to claim 1 wherein the treatment does not include rinsing off the cleansing composition with water from the skin or hair.

* * * * *